(12) United States Patent
Mainx et al.

(10) Patent No.: US 9,226,497 B2
(45) Date of Patent: Jan. 5, 2016

(54) AGRICULTURAL COMPOSITIONS

(75) Inventors: Hans-Georg Mainx, Leichlingen (DE); Ingo Fleute-Schlachter, Essen (DE); Stefan Busch, Düsseldorf (DE); Sandra Mack, Korschenbroich (DE)

(73) Assignee: Cognis IP Management GmbH, Duesseldorf (DE)

( * ) Notice: Subject to any disclaimer, the term of this patent is extended or adjusted under 35 U.S.C. 154(b) by 273 days.

(21) Appl. No.: 13/382,567

(22) PCT Filed: Jun. 29, 2010

(86) PCT No.: PCT/EP2010/003936
§ 371 (c)(1),
(2), (4) Date: Jan. 6, 2012

(87) PCT Pub. No.: WO2011/003534
PCT Pub. Date: Jan. 13, 2011

(65) Prior Publication Data
US 2012/0115730 A1 May 10, 2012

(30) Foreign Application Priority Data
Jul. 8, 2009 (EP) .................................... 09008892

(51) Int. Cl.
*A01N 25/30* (2006.01)
(52) U.S. Cl.
CPC ...................................... *A01N 25/30* (2013.01)
(58) Field of Classification Search
CPC ...................................................... A01N 25/30
See application file for complete search history.

(56) References Cited

U.S. PATENT DOCUMENTS

| 4,389,213 A * | 6/1983 | Schneider et al. ................. 8/524 |
| 2002/0137634 A1 | 9/2002 | Krause et al. |
| 2008/0312290 A1 | 12/2008 | Vermeer et al. |

FOREIGN PATENT DOCUMENTS

| DE | 1243312 B | * | 6/1967 |
| DE | 102007013363 | | 9/2008 |
| EP | 1427280 | | 12/2004 |
| JP | 62-148285 A | * | 7/1987 |
| RU | 2248126 | | 3/2005 |
| WO | WO-99/27782 | | 6/1999 |
| WO | WO-01/20986 | | 3/2001 |

OTHER PUBLICATIONS

Danuta Wlasiuk, Gabriela Dziala and Alojzy Klopotek, "Properties of new multifunctional detergents", Przemysl Chemiczny (1985), 64(11), 543-4 (Abstract only).*
Alojzy Klopotek, Danuta Wlasiuk and Gabriela Dziala, "Synthesis and useful properties of some new polyfunctional copolymers", Polimery (Warsaw, Poland) (1985), 30(4), 148-51 (Abstract only).*
"PCT International Search Report for PCT/EP2010/003936", May 2, 2011, 4 pages.

* cited by examiner

*Primary Examiner* — John Pak
*Assistant Examiner* — Nathan W Schlientz
(74) *Attorney, Agent, or Firm* — Servilla Whitney LLC

(57) ABSTRACT

Described are agrochemical compositions comprising alkoxylation products according to general formula (I)

$$R^1(CO)_m-O-[R^2O]_nR^3 \qquad (I)$$

wherein $R^1$ is a linear or branched, saturated or unsaturated, optionally hydroxy-functionalized hydrocarbyl radical containing 8 to 30 carbon atoms, $R^2$ is an ethylene, propylene or butylene group or mixtures thereof, $R^3$ is hydrogen or an acyl group containing 1 to 8 carbon atoms, m is 0 or 1, n is an integer between 3 and 100. When $R^3$ is an acyl group, $R^2$ is ethylene, propylene or mixtures thereof, and when $R^3$ is hydrogen, $R^2$ is ethylene, propylene, butylene or mixtures thereof provided that the terminal group represents a butylene oxide unit.

13 Claims, No Drawings

AGRICULTURAL COMPOSITIONS

CROSS-REFERENCE TO RELATED APPLICATIONS

This application is the National Stage entry of PCT/EP2010/003936, filed on Jun. 29, 2010, which claims priority to European Patent application number 09008892.3, filed on Jul. 8, 2009, both of which are incorporated herein by reference in their entireties.

TECHNICAL FIELD

The present invention is related to the area of agriculture and refers to compositions comprising new alkoxylation products of fatty alcohols and/or fatty acids, a method for treating plants and the use of said new alkoxylation products for a variety of agricultural purposes.

BACKGROUND

Biocides, and in particular pesticides such as fungicides, insecticides and herbicides, are important auxiliary agents for agriculture in order to protect crops and to increase their quality and harvest yield. Depending on the various and often very specific needs, a magnitude of actives exists which shows very different chemical structures and behaviours. Nevertheless, it is well known from the state of the art that it remains difficult to prepare solid or even liquid compositions of these actives which are exhibiting a satisfying stability, especially if stored at very low or elevated temperatures over a longer period. In addition to storage stability and the ability to prepare stable tank mixes, the influence of additives and adjuvants on bio-performance is of elevated importance. Their choice is governed by many additional parameters, such as ease to manufacture, a low toxicological and ecotoxicological profile, their compatibility such formulations such as emulsifiable concentrates (EC), oil in water emulsions (EW), suspo-emulsions (SE) and concentrated suspensions in water (SC) or in oil (OD)

In order to meet requirements outlined above one can find various additives in the market. For example international application WO 99/027782 A1 (Henkel) claims adjuvants which are obtained from adducts of up to 10 ethylene oxide (EO) and/or propylene oxide (PO) units, end capped by $C_1$ to $C_{12}$ alkyl radicals. Syngenta's patent EP 1427280 B1 refers to Oleyl alkoxylates comprising typically about 20 moles EO or PO, preferably end-capped by butyl groups. The use of butyl chloride for capping the alkoxylate, however, is disadvantageous since the formation of butene as a side-reaction requires an excess of the butyl chloride. For application and environmental reasons, this is an undesired effect.

The problem underlying the present invention has been to overcome the disadvantages of the state of the art. In particular it has been the object to provide new additives for agricultural compositions fulfilling a complex profile of application requirements: adjuvant properties in order to support and increase the performance of the biocides within the compositions, high stability of the compositions also over longer storage times and different storage temperatures, compatibility with a wide range of biocides, and low foaming behavior.

SUMMARY

Embodiments of the present invention are directed toward agrochemical compositions comprising alkoxylation products according to general Formula (I)

$R^1(CO)_m$—$O[R^2O]_nR^3$ (I), wherein $R^1$ is a linear or branched, saturated or unsaturated, optionally hydroxyl-functionalized hydrocarbyl radical containing 6 to 30 carbon atoms, $R^2$ is an ethylene, propylene or butylene group or mixtures thereof, $R^3$ is hydrogen or an acyl group containing 1 to 8 carbon atoms, m is 0 or 1, and n is an integer between 3 and 100. When $R^3$ is an acyl group, $R^2$ is ethylene, propylene, or mixtures thereof. When $R^3$ is hydrogen, $R^2$ is ethylene, propylene, butylene or mixtures thereof, provided that the terminal group represents a butylene oxide unit.

In one or more embodiments, $R^1$ contains 8 to 22 carbon atoms. $R_1$ can represent an unsaturated hydrocarbyl radical.

In a specific embodiment, $R^1$ represents an oleyl radical and m is zero.

In one or more embodiments, $R^3$ represents an acyl group having 2, 3, or 8 carbon atoms.

In one or more embodiments, n is an integer between 5 and 30.

In or more embodiments, the compositions further comprise biocides. The biocides can be selected from the group consisting of herbicides, insecticides, fungicides, miticides, and plant growth promoters.

In a specific embodiment, the compositions further comprise biocides selected from those having a systemic or semi-systemic mode of action. The biocides can have a water solubility of less than 600 ppm.

In one or more embodiments, the agrochemical compositions comprise by weight based on the total composition: 0.1 to 50% alkoxylation products according to general Formula (I), 20 to 99.9% biocides, 0 to 20% oil components, 0 to 10% emulsifiers, and 0 to 50% solvents, where the total amounts add to give 100%.

Other embodiments of the present invention are directed to a method of treating plants, the method comprising spraying an agrochemical composition according to the present invention onto the plants or onto the immediate environment of the plants.

A further embodiment of the present invention is direct to a method for treating seeds, the method comprising using an agrochemical composition according to the present invention as a seed coating. The composition can further comprise a biocide selected from the group consisting of insecticides, miticides, fungicides, nematicides, and rhodenticides.

Other embodiments of the present invention are directed to methods of making agricultural compositions, the method comprising using the alkoxylation products of the present invention are adjuvants or as tank mix additives.

DETAILED DESCRIPTION

The present invention refers to agrochemical compositions comprising alkoxylation products according to general formula (I)

$$R^1(CO)_m\text{—}O\text{—}[R^2O]_nR^3 \qquad (I)$$

wherein
  $R^1$ is a linear or branched, saturated or unsaturated, optionally hydroxy-functionalised hydrocarbyl radical containing 8 to 30 carbon atoms,
  $R^2$ means an ethylene, propylene or butylene group or their mixtures,
  $R^3$ means hydrogen or an acyl group containing 1 to 8 carbon atoms
  m is 0 or 1,
  n stands for an integer between 3 and 100, on condition that in case $R^3$ stands for an acyl group, $R^2$ is ethylene, propylene or their mixtures, and in case $R^3$ stands for hydrogen, $R^2$ is ethylene, propylene, butylene or their mixtures provided that the terminal group represents a butylene oxide unit.

For people skilled in the art it is known that a low static surface tension of spray solutions is usually attributed to better leaf uptake of active ingredients. This physical property is primarily influenced by the additive or adjuvant. The alkoxylation products according to the present invention show a higher surface tension than those additives well known from the state of the art. Surprisingly it has been observed that the alkoxylation products according to the present invention exhibit increased adjuvant properties when compared with very similar additives well known from the state of the art.

Alkoxylation Products

Alkoxylation products (component a) according to the present invention represent well known compounds obtainable by standard operations of organic chemistry. More particular the alkoxylation products are obtained either from fatty acids or fatty alcohols, representing adducts of ethylene oxide, propylene oxide and/or butylene oxide, end-capped by acyl groups or not. Preferably, the hydrophobic part of the molecule is derived from fatty acids or fatty alcohols having 12 to 22 carbon atoms, which means that preferably $R^1$ contains 11 to 21 carbon atoms. Suitable fatty acids are chosen from the group consisting of capronic acid, caprylic acid, caprinic acid, lauric acid, myristic acid, palmitic acid, palmoleic acid, stearic acid, isostearic acid, oleic acid, elaidinic acid, linoic acid, linolenic acid, 12-hydroxy stearic acid, ricinoleic acid, gadoleic acid, arachidonic acid, behenic acid, erucic acid and their technical mixtures, like for example coco fatty acid, palm fatty acid, tallow fatty acid, sunflower fatty acid, soy fatty acid and the like. Suitable fatty alcohols are the ones corresponding to the fatty acids explained above. Rather advantageous alkoxylation products are fully or in part unsaturated and follow general formula (I) in which $R^1$ represents an unsaturated hydrocarbyl radical. More particular preferred are species in which $R^1$ represents an oleyl radical and m is zero or $R^1(CO)_m$ stands for an oleic acid radical and m is 1. It is not necessary that component (a) is fully derived from unsaturated species; on a case by case basis it may be even more advantageous to chose mixtures of saturated and unsaturated starting materials, which can be defined by their iodine value, which may range from 50 to 95.

The fatty alcohols or fatty acids are subjected to alkoxylation according to standard procedures of organic chemistry. The degree of alkoxylation expressed by the value "n" may range from 3 to 100; preferably it lies between 5 and 30, more preferably between 10 and 20. Alkoxylation may take place blockwise or in random distribution. That means, that one either adds ethylene oxide to the acid or the alcohol, followed by propylene oxide and/or butylene oxide or use a mixture of the two or three components. In case non-capped alkoxylation products are used it has been found crucial that the final group of the polyalkylene glycol ether chain is a butylene oxide unit.

In a specific embodiment of the present invention the alkoxylation products thus obtained may be end-capped by alkylation using certain acylation agents. Typically the C-chain of these acylation agents may vary from 2 to 8, preferred examples are alkoxylation products end-capped by $C_2$, $C_3$ or $C_8$ acyl radicals. Overall preferred alkoxylation products are adducts of Oleyl alcohol or oleic acid, having iodine values of 50 to 95, comprising 10 to 20 EO units and optionally at least one BO unit, optionally end-capped by acetic acid, propionic acid or capronic acid.

Biocides

A biocide (component b) in the context of the present invention is a plant protection agent, more particular a chemical substance capable of killing different forms of living organisms used in fields such as medicine, agriculture, forestry, and mosquito control. Also counted under the group of biocides are so-called plant growth regulators. Usually, biocides are divided into two sub-groups:

pesticides, which includes fungicides, herbicides, insecticides, algicides, moluscicides, miticides and rodenticides, (here, The Pesticide Manual, 14th edition, BCPC 2006 is included as a reference, it provides information about the individual mode of actions of active ingredients) and antimicrobials, which includes germicides, antibiotics, antibacterials, antivirals, antifungals, antiprotozoals and antiparasites.

Biocides can also be added to other materials (typically liquids) to protect the material from biological infestation and growth. For example, certain types of quaternary ammonium compounds (quats) can be added to pool water or industrial water systems to act as an algicide, protecting the water from infestation and growth of algae.

Pesticides

The U.S. Environmental Protection Agency (EPA) defines a pesticide as "any substance or mixture of substances intended for preventing, destroying, repelling, or mitigating any pest". A pesticide may be a chemical substance or biological agent (such as a virus or bacteria) used against pests including insects, mites, plant pathogens, weeds, mollusks, birds, mammals, fish, nematodes (roundworms) and microbes that compete with humans for food, destroy property, spread disease or are a nuisance. In the following examples, pesticides suitable for the agrochemical compositions according to the present invention are given:

Fungicides. A fungicide is one of three main methods of pest control—the chemical control of fungi in this case. Fungicides are chemical compounds used to prevent the spread of fungi in gardens and crops. Fungicides are also used to fight fungal infections. Fungicides can either be contact or systemic. A contact fungicide kills fungi when sprayed on its surface. A systemic fungicide has to be absorbed by the fungus before the fungus dies. Examples for suitable fungicides, according to the present invention, encompass the following chemical classes and corresponding examples:

Aminopyrimidines such as bupirimate,

Anilinopyrimidines such as cyprodinil, mepanipyrim, pyrimethanil,

Heteroaromatics such as hymexazol,

Heteroaromatic hydrocarbons such as etridiazole,

Chlorophenyls/Nitroanilines such as chloroneb, dicloran, quintozene, tecnazene, tolclofos-methyl, Benzamide fungicides such as zoxamide, Benzenesulfonamides such as flusulfamide, Benzimidazoles such as acibenzolar, benomyl, benzothiazole, carbendazim, fuberidazole, metrafenone, probenazole, thiabendazole, triazoxide, and benzimidazole precursor fungicides, Carbamates such as propamocarb, diethofencarb, Carboxamides such as boscalid, diclocymet, ethaboxam, flutolanil, penthiopyrad, thifluzamide Chloronitriles such chlorothalonil, Cinnamic acid amides such as dimethomorph, flumorph, Cyanoacetamide oximes such as cymoxanil, Cyclopropancarboxamides such as carpropamid, Dicarboximides such as iprodione, octhilinone, procymidone, vinclozolin
Dimethyldithiocarbamates such ferbam, metam, thiram, ziram,
Dinitroanilines such as fluazinam,
Dithiocarbamates such as mancopper, mancozeb, maneb, metiram, nabam, propineb, zineb,
Dithiolanes such as isoprothiolane,
Glucopyranosyl antibiotics such as streptomycin, validamycin,
Guanidines such as dodine, guazatine, iminoctadine,
Hexopyranosyl antibiotics such as kasugamycin,
Hydroxyanilides such as fenhexamid,
Imidazoles such as imazalil, oxpoconazole, pefurazoate, prochloraz, triflumizole,
Imidazolinones such as fenamidone,
Inorganics such as Bordeaux mixture, copper hydroxide, copper naphthenate, copper oleate, copper oxychloride, copper(II) sulfate, copper sulfate, copper(II) acetate, copper(II) carbonate, cuprous oxide, sulfur,
Isobenzofuranones such as phthalide,
Mandelamides such as mandipropamide,
Morpholines such as dodemorph, fenpropimorph, tridemorph, fenpropidin, piperalin, spiroxamine, aldimorph
Organotins such as fentin,
Oxazolidinones such as oxadixyl,
Phenylamides such as benalaxyl, benalaxyl-M, furalaxyl, metalaxyl, metalaxyl-M, ofurace,
Phenylpyrazoles such as fipronil,
Phenylpyrroles such as fludioxonil,
Phenylureas such as pencycuron,
Phosphonates such fosetyl,
Phthalamic acids such as tecloftalam,
Phthalimides such as captafol, captan, folpet,
piperazines such as triforine,
Propionamides such as fenoxanil,
Pyridines such as pyrifenox,
Pyrimidines such as fenarimol, nuarimol,
Pyrroloquinolinones such as pyroquilon,
Qils such as cyazofamid,
Quinazolinones such as proquinazid,
Quinolines such as quinoxyfen,
Quinones such as dithianon,
Sulfamides such as tolylfluanid, dichiofluanid,
Strobilurines such as azoxystrobin, dimoxystrobin, famoxadone, fluoxastrobin, kresoxim-methyl, metominostrobin, picoxystrobin, pyraclostrobin, trifloxystrobin, orysastrobin,
Thiocarbamates such as methasulfocarb,
Thiophanates such as thiophanate-methyl,
Thiophencarboxamides such silthiofam,
Triazole fungicides such as azaconazole, bitertanol, bromuconazole, cyproconazole, difenoconazole, diniconazole, epoxiconazole, fenbuconazole, fluquinconazole, flusilazole, flutriafol, fluotrimazole, hexaconazole, imibenconazole, ipconazole, metconazole, myclobutanil, penconazole, propiconazole, prothioconazole, simeconazole, tebuconazole, tetraconazole, triadimefon, triadimenol, triticonazole, quinconazole
Triazolobenzothidazoles such as tricyclazole,
Valinamide carbamates such as iprovalicarb, benthiavalicarb
Fluopicolide
and their mixtures.

Herbicides. An herbicide is a pesticide used to kill unwanted plants. Selective herbicides kill specific targets while leaving the desired crop relatively unharmed. Some of these act by interfering with the growth of the weed and are often based on plant hormones. Herbicides used to clear waste ground are nonselective and kill all plant material with which they come into contact. Herbicides are widely used in agriculture and in landscape turf management. They are applied in total vegetation control (TVC) programs for maintenance of highways and railroads. Smaller quantities are used in forestry, pasture systems, and management of areas set aside as wildlife habitat. In general, active ingredients representing including various chemical classes and corresponding examples can be used
Anilides such as propanil
Aryloxycarboxylic acids e.g. MCPA-thioethyl
Aryloxyphenoxypropionates e.g. clodinafop-propargyl, cyhalofop-butyl, diclofops, fluazifops, haloxyfops, quizalofops,
Chloroacetamides e.g. acetolochlor, alachlor, butachlor, dimethenamid, metolachlor, propachlor
Cyclohexanedione oximes e.g. clethodim, sethoxydim, tralkoxydim,
Benzamides such as isoxaben
Benzimidazoles such as dicamba, ethofumesate
Dinitroanilines e.g. trifluralin, pendimethalin,
Diphenyl ethers e.g. aclonifen, oxyfluorfen,
The glycine derivative glyphosate, a systemic nonselective (it kills any type of plant) herbicide used in no-till burndown and for weed control in crops that are genetically modified to resist its effects,
Glufosinate
Hydroxybenzonitriles e.g. bromoxynil,
Imidazolinones e.g. fenamidone, imazapic, imazamox, imazapic, imazapyr, imazaquin,
Isoxazolidinones e.g. clomazone
Paraquat as bypyridylium,
Phenyl carbamates e.g. desmedipham, phenmedipham,
Phenylpyrazoles e.g. pyraflufen-ethyl
Phenylpyrazolines e.g. pinoxaden,
Pyridinecarboxylic acids or synthetic auxins e.g. picloram, clopyralid, and triclopyr,
Pyrimidinyloxybenzoics e.g. bispyrtbac-sodium
Sulfonyureas e.g. amidosulfuron, azimsulfuron, bensulfuron-methyl, chlorsulfuron, flazasulfuron, foramsulfuron, flupyrsulfuron-methyl-sodium, nicosulfuron, rimsulfuron, sulfosulfuron, tribenuron-methyl, trifloxysurlfuron-sodium, triflusulfuron, tritosulfuron,
Triazolopyrimidines e.g. penoxsulam, metosulam, florasulam,
Triketones e.g. mesotriones, sulcotrione,
Ureas e.g. diuron, linuron,
Phenoxycarboxylic acids such as 2,4-D, MCPA, MCPB, mecoprops,
Triazines such as atrazine, simazine, terbuthylazine,
and their mixtures.

Insecticides. An insecticide is a pesticide used against insects in all developmental forms. They include ovicides and larvicides used against the eggs and larvae of insects. Insecticides are used in agriculture, medicine, industry and the household. In the following, suitable chemical classes and examples of insecticides are mentioned:
Avermectin derivatives such as Abamectin, emamectin,
Anthranilic diamides such as rynaxypyr
Synthetic auxins Duch as avermectin,
Amidines such as amitraz,
Anthranilic diamide Duch as rynaxypyr,
Carbamates such as aldicarb, carbofuran, carbaryl, methomyl, 2-(1-methylpropyl)phenyl methylcarbamate, Chlorinated insecticides such as, for example, Camphechlor, DDT, Hexachlorocyclohexane, gamma-Hexachlorocyclohexane, Methoxychlor, Pentachlorophenol, TDE, Aldrin, Chlordane, Chlordecone, Dieldrin, Endosulfan, Endrin, Heptachlor, Mirex, Juvenile hormone mimics such as pyriproxyfen, Neonicotinoids such as imidacloprid, clothianidin, thiacloprid, thiamethoxam, Organophosphorus compounds such as acephate, azinphos-methyl, bensulide, chlorethoxyfos, chlorpyrifos, chlorpyriphos-methyl, diazinon, dichlorvos (DDVP), dicrotophos, dimethoate, disulfoton, dthoprop, fenamiphos, fenitrothion, fenthion, fosthiazate, malathion, methamidophos, methidathion, methyl-parathion, mevinphos, naled, omethoate, oxydemeton-methyl, parathion, phorate, phosalone, phosmet, phostebupirim, pirimiphos-methyl, profenofos, terbufos, tetrachlorvinphos, tribufos, trichlorfon, Oxadiazines such as indoxacarb, Plant toxin derived compounds such as derris (rotenone), pyrethrum, neem (azadirachtin), nicotine, caffeine, Pheromones such cuellure, methyl eugenol, Pyrethroids such as, for example, allethrin, bifenthrin, deltamethrin, permethrin, resmethrin, sumithrin, tetramethrin, tralomethrin, transfluthrin, Selective feeding blockers such as flonicamid, pymetrozine, Spinosyns e.g. spinosad and their mixtures.

Plant Growth Regulators. Plant hormones (also known as phytohormones) are chemicals that regulate plant growth. Plant hormones are signal molecules produced within the plant, and occur in extremely low concentrations. Hormones regulate cellular processes in targeted cells locally and when moved to other locations, in other locations of the plant. Plants, unlike animals, lack glands that produce and secrete hormones. Plant hormones shape the plant, affecting seed growth, time of flowering, the sex of flowers, senescence of leaves and fruits. They affect which tissues grow upward and which grow downward, leaf formation and stem growth, fruit development and ripening, plant longevity and even plant death. Hormones are vital to plant growth and lacking them, plants would be mostly a mass of undifferentiated cells. In the following, suitable plant growth regulators are mentioned:

Aviglycine,

Cyanamide,

Gibberellins such gibberellic acid,

Quaternary ammoniums such as chlormequat chloride, mepiquat chloride,

Ethylene generators such ethephone,

Rodenticides. Rodenticides are a category of pest control chemicals intended to kill rodents. Rodents are difficult to kill with poisons because their feeding habits reflect their place as scavengers. They would eat a small bit of something and wait, and if they do not get sick, they would continue eating. An effective rodenticide must be tasteless and odorless in lethal concentrations, and have a delayed effect. In the following, examples for suitable rodenticides are given:

Anticoagulants are defined as chronic (death occurs after 1-2 weeks post ingestion of the lethal dose, rarely sooner), single-dose (second generation) or multiple dose (first generation) cumulative rodenticides. Fatal internal bleeding is caused by lethal dose of anticoagulants such as brodifacoum, coumatetralyl or warfarin. These substances in effective doses are antivitamins K, blocking the enzymes $K_1$-2,3-epoxide-reductase (this enzyme is preferentially blocked by 4-hydroxycoumarin/4-hydroxythiacoumarin derivatives) and $K_1$-quinone-reductase (this enzyme is preferentially blocked by indandione derivatives), depriving the organism of its source of active vitamin $K_1$. This leads to a disruption of the vitamin K cycle, resulting in an inability of production of essential blood-clotting factors (mainly coagulation factors II (prothrombin), VII (proconvertin), IX (Christmas factor) and X (Stuart factor)). In addition to this specific metabolic disruption, toxic doses of 4-hydroxycoumarin/4-hydroxythiacoumarin and indandione anticoagulants are causing damage to tiny blood vessels (capillaries), increasing their permeability, causing diffuse internal bleedings (haemorrhagias). These effects are gradual; they develop in the course of days and are not accompanied by any nociceptive perceptions, such as pain or agony. In the final phase of intoxication the exhausted rodent collapses in hypovolemic circulatory shock or severe anemia and dies calmly. Rodenticidal anticoagulants are either first generation agents (4-hydroxycoumarin type: warfarin, coumatetralyl; indandione type: pindone, diphacinone, chlorophacinone), generally requiring higher concentrations (usually between 0.005 and 0.1%), consecutive intake over days in order to accumulate the lethal dose, poor active or inactive after single feeding and less toxic than second generation agents, which are derivatives of 4-hydroxycoumarin (difenacoum, brodifacoum, bromadiolone and flocoumafen) or 4-hydroxy-1-benzothiin-2-one (4-hydroxy-1-thiacoumarin, sometimes incorrectlly referred to as 4-hydroxy-1-thiocoumarin, for reason see heterocyclic compounds), namely difethialone. Second generation agents are far more toxic than first generation agents, they are generally applied in lower concentrations in baits (usually in the order of 0.001-0.005%), and are lethal after single ingestion of bait and are effective also against strains of rodents that have become resistant against first generation anticoagulants; thus the second generation anticoagulants are sometimes referred to as "superwarfarins". Sometimes, anticoagulant rodenticides are potentiated by an antibiotic, most commonly by sulfaquinoxaline. The aim of this association (e.g. warfarin 0.05%+sulfaquinoxaline 0.02%, or difenacoum 0.005%+sulfaquinoxaline 0.02% etc.) is that the antibiotic/bacteriostatic agent suppresses intestinal/gut symbiotic microflora that represents a source of vitamin K. Thus the symbiotic bacteria are killed or their metabolism is impaired and the production of vitamin K by them is diminuted, an effect which logically contributes to the action of anticoagulants. Antibiotic agents other than sulfaquinoxaline may be used, for example co-trimoxazole, tetracycline, neomycin or metronidazole. A further synergism used in rodenticidal baits is that of an association of an anticoagulant with a compound with vitamin D-activity, i.e. cholecalciferol or ergocalciferol (see below). A typical formula used is, e.g., warfarin 0.025-0.05%+cholecalciferol 0.01%. In some countries there are even fixed three-component rodenticides, i.e. anticoagulant+antibiotic+vitamin D, e.g. difenacoum 0.005%+sulfaquinoxaline 0.02%+cholecalciferol 0.01%. Associations of a second-generation anticoagulant with an antibiotic and/or vitamin D are considered to be effective even against the most resistant strains of rodents, though some second generation anticoagulants (namely brodifacoum and difethialone), in bait concentrations of 0.0025-0.005% are so toxic that no known resistant strain of rodents exists and even rodents resistant against any other derivatives are reliably exterminated by application of these most toxic anticoagulants.

Vitamin $K_1$ has been suggested and successfully used as an antidote for pets or humans, which/who were either accidentally or intentionally (poison assaults on pets, suicidal attempts) exposed to anticoagulant poisons. In addition, since some of these poisons act by inhibiting liver functions and in progressed stages of poisoning, several blood-clotting factors as well as the whole volume of circulating blood lacks, a blood transfusion (optionally with the clotting factors present) can save a person's life who inadvertently takes them, which is an advantage over some older poisons.

Metal phosphides have been used as a means of killing rodents and are considered single-dose fast acting rodenticides (death occurs commonly within 1-3 days after single bait ingestion). A bait consisting of food and a phosphide (usually zinc phosphide) is left where the rodents can eat it. The acid in the digestive system of the rodent reacts with the phosphide to generate the toxic phosphine gas. This method of vermin control has possible use in places where rodents are resistant to some of the anticoagulants, particularly for control of house and field mice; zinc phosphide baits are also cheaper than most second-generation anticoagulants, so that sometimes, in cases of large infestation by rodents, their population is initially reduced by copious amounts of zinc phosphide bait applied, and the rest of the population that survived the initial fast-acting poison is then eradicated by prolonged feeding on anticoagulant bait. Inversely, the individual rodents that survived anticoagulant bait poisoning (rest population) can be eradicated by pre-baiting them with nontoxic bait for a week or two (this is important to overcome bait shyness, and to get rodents used to feeding in specific areas by offering specific food, especially when eradicating rats) and subsequently applying poisoned bait of the same sort as used for pre-baiting until all consumption of the bait ceases (usually within 2-4 days). These methods of alternating rodenticides with different modes of action provides a factual or an almost 100% eradication of the rodent population in the area if the acceptance/palatability of bait is good (i.e., rodents readily feed on it).

Phosphides are rather fast acting rat poisons, resulting in that the rats are dying usually in open areas instead of the affected buildings. Typical examples are aluminum phosphide (fumigant only), calcium phosphide (fumigant only), magnesium phosphide (fumigant only) and zinc phosphide (in baits). Zinc phosphide is typically added to rodent baits in amounts of around 0.75-2%. The baits have a strong, pungent garlic-like odor characteristic for phosphine liberated by hydrolysis. The odor attracts (or, at least, does not repulse) rodents, but has a repulsive effect on other mammals; birds, however (notably wild turkeys), are not sensitive to the smell and feed on the bait thus becoming collateral damage.

Hypercalcemia. Calciferols (vitamins D), cholecalciferol (vitamin $D_3$) and ergocalciferol (vitamin $D_2$) are used as rodenticides, which are toxic to rodents for the same reason that they are beneficial to mammals: they are affecting calcium and phosphate homeostasis in the body. Vitamins D are essential in minute quantities (few IUs per kilogram body weight daily, which is only a fraction of a milligram), and like most fat soluble vitamins they are toxic in larger doses as they readily result in the so-called hypervitaminosis, which is, simply said, poisoning by the vitamin. If the poisoning is severe enough (that is, if the dose of the toxicant is high enough), it eventually leads to death. In rodents consuming the rodenticidal bait it causes hypercalcemia by raising the calcium level, mainly by increasing calcium absorption from food, mobilising bone-matrix-fixed calcium into ionised form (mainly monohydrogencarbonate calcium cation, partially bound to plasma proteins, $[CaHCO_3]^+$), which circulates dissolved in the blood plasma, and after ingestion of a lethal dose the free calcium levels are raised sufficiently so that blood vessels, kidneys, the stomach wall and lungs are mineralised/calcificated (formation of calcificates, crystals of calcium salts/complexes in the tissues thus damaging them), leading further to heart problems (myocard is sensitive to variations of free calcium levels that are affecting both myocardial contractibility and excitation propagation between atrias and ventriculas) and bleeding (due to capillary damage) and possibly kidney failure. It is considered to be single-dose, or cumulative (depending on concentration used; the common 0.075% bait concentration is lethal to most rodents after a single intake of larger portions of the bait), sub-chronic (death occurring usually within days to one week after ingestion of the bait). Applied concentrations are 0.075% cholecalciferol and 0.1% ergocalciferol when used alone. There is an important feature of calciferols toxicology which is that they are synergistic with anticoagulant toxicants. This means that mixtures of anticoagulants and calciferols in the same bait are more toxic than the sum of toxicities of the anticoagulant and the calciferol in the bait so that a massive hypercalcemic effect can be achieved by a substantially lower calciferol content in the bait and vice-versa. More pronounced anticoagulant/hemorrhagic effects are observed if calciferol is present. This synergism is mostly used in baits low in calciferol because effective concentrations of calciferols are more expensive than effective concentrations of most anticoagulants. The historically very first application of a calciferol in rodenticidal bait was, in fact, the Sorex product Sorexa® D (with a different formula than today's Sorexa® D) back in the early 1970's, containing warfarin 0.025%+ergocalciferol 0.1%. Today, Sorexa® CD contains a 0.0025% difenacoum+0.075% cholecalciferol combination. Numerous other brand products containing either calciferols 0.075-0.1% (e.g. Quintox®, containing 0.075% cholecalciferol) alone, or a combination of calciferol 0.01-0.075% with an anticoagulant are marketed.

Miticides, moluscicides and nematicides. Miticides are pesticides that kill mites. Antibiotic miticides, carbamate miticides, formamidine miticides, mite growth regulators, organochlorine, permethrin and organophosphate miticides all belong to this category. Molluscicides are pesticides used to control mollusks, such as moths, slugs and snails. These substances include metaldehyde, methiocarb and aluminium sulfate. A nematicide is a type of chemical pesticide used to kill parasitic nematodes (a phylum of worm). A nematicide is obtained from a neem tree's seed cake; which is the residue of neem seeds after oil extraction. The neem tree is known by several names in the world but was first cultivated in India since ancient times.

Antimicrobials

In the following examples, antimicrobials suitable for agrochemical compositions according to the present invention are given. Bactericidal disinfectants mostly used are those applying active chlorine (i.e., hypochlorites, chloramines, dichloroisocyanurate and trichloroisocyanurate, wet chlorine, chlorine dioxide, etc.), active oxygen (peroxides such as peracetic acid, potassium persulfate, sodium perborate, sodium percarbonate and urea perhydrate), iodine (iodpovidone (povidone-iodine, Betadine), Lugol's solution, iodine tincture, iodinated nonionic surfactants), concentrated alcohols (mainly ethanol, 1-propanol, called also n-propanol and 2-propanol, called isopropanol and mixtures thereof; further, 2-phenoxyethanol and 1- and 2-phenoxypropanols are used), phenolic substances (such as phenol (also called "carbolic acid"), cresols (called "Lysole" in combination with liquid potassium soaps), halogenated (chlorinated, brominated) phenols, such as hexachlorophene, triclosan, trichlorophenol, tribromophenol, pentachlorophenol, Dibromol and salts thereof), cationic surfactants such as some quaternary ammonium cations (such as benzalkonium chloride, cetyl trimethylammonium bromide or chloride, didecyldimethylammonium chloride, cetylpyridinium chloride, benzethonium chloride) and others, non-quarternary compounds such as chlorhexidine, glucoprotamine, octenidine dihydrochloride, etc.), strong oxidizers such as ozone and permanganate solutions;

heavy metals and their salts such as colloidal silver, silver nitrate, mercury chloride, phenylmercury salts, copper sulfate, copper oxide-chloride etc. Heavy metals and their salts are the most toxic and environmentally hazardous bactericides and, therefore, their use is strongly suppressed or forbidden; further, also properly concentrated strong acids (phosphoric, nitric, sulfuric, amidosulfuric, toluenesulfonic acids) and alcalis (sodium, potassium, calcium hydroxides) between pH<1 or >13, particularly below elevated temperatures (above 60° C.) kill bacteria.

As antiseptics (i.e., germicide agents that can be used on human or animal body, skin, mucoses, wounds and the like), few of the above mentioned disinfectants can be used under proper conditions (mainly concentration, pH, temperature and toxicity toward man/animal). Among them, important are Some properly diluted chlorine preparations (e.g. Daquin's solution, 0.5% sodium or potassium hypochlorite solution, pH-adjusted to pH 7-8, or 0.5-1% solution of sodium benzenesulfochloramide (chloramine B)), some iodine preparations such as iodopovidone in various galenics (ointments, solutions, wound plasters), in the past also Lugol's solution, peroxides as urea perhydrate solutions and pH-buffered 0.1-0.25% peracetic acid solutions, alcohols with or without antiseptic additives, used mainly for skin antisepsis, weak organic acids such as sorbic acid, benzoic acid, lactic acid and salicylic acid some phenolic compounds such as hexachlorophene, triclosan and Dibromol, and cation-active compounds such as 0.05-0.5% benzalkonium, 0.5-4% chlorhexidine, 0.1-2% octenidine solutions.

Bactericidal antibiotics kill bacteria; bacteriostatic antibiotics only slow down their growth or reproduction. Penicillin is a bactericide, as are cephalosporins. Aminoglycosidic antibiotics can act in both a bactericidic manner (by disrupting cell wall precursor leading to lysis) or bacteriostatic manner (by connecting to 30s ribosomal subunit and reducing translation fidelity leading to inaccurate protein synthesis). Other bactericidal antibiotics according to the present invention include the fluoroquinolones, nitrofurans, vancomycin, monobactams, co-trimoxazole, and metronidazole Preferred actives are those with systemic or partially systemic mode of action such as for example azoxystrobin.

Overall preferred biocides belong to the groups of herbicides, insecticides, fungicides, miticides, and plant growth promoters, in particular showing a systemic or semi-systemic mode of action and/or having a water solubility of less than 600 ppm. In particular preferred are glyphosate, glufosinate, its salts and derivatives.

Oil Components

In a number of cases it is advantageous to add oil components (optional component c) to the biocide compositions in order to support the emulsification power of the products. Suitable products comprise Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxy carboxylic acids with linear or branched $C_6$-$C_{22}$-fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms (Cetiol® B) or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Cetiol® AB), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.), aliphatic or naphthenic hydrocarbons, such as, for example, squalane, squalene or dialkylcyclohexanes, and/or mineral oils. The preferred oil components/cosolvents show an ester structure preferably adipates (Cetiol® B, Agnique DiME 6), methyl esters of vegetable oils (Agnique® ME 18RD-F, Agnique®

ME 12C-F), alkyl esters (Agnique® Ae 3-2EH), all products available in the market from Cognis GmbH.

Emulsifiers

In a number of cases it is advantageous to add emulsifiers (optional component d) to the biocide compositions in order to support the stability of the products. A first preferred group of emulsifiers encompasses non-ionic surfactants such as, for example:

- products of the addition of 2 to 30 mol ethylene oxide and/or 0 to 5 mol propylene oxide onto linear $C_{8-22}$ fatty alcohols, onto $C_{12-22}$ fatty acids and onto alkyl phenols containing 8 to 15 carbon atoms in the alkyl group;
- $C_{12/18}$ fatty acid monoesters and diesters of addition products of 1 to 30 mol ethylene oxide onto glycerol;
- glycerol mono- and diesters and sorbitan mono- and diesters of saturated and unsaturated fatty acids containing 6 to 22 carbon atoms and ethylene oxide addition products thereof;
- addition products of 15 to 60 mol ethylene oxide onto castor oil and/or hydrogenated castor oil;
- polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;
- addition products of 2 to 15 mol ethylene oxide onto castor oil and/or hydrogenated castor oil;
- partial esters based on linear, branched, unsaturated or saturated $C_{6/22}$ fatty acids, ricinoleic acid and 12-hydroxystearic acid and glycerol, polyglycerol, pentaerythritol, -dipentaerythritol, sugar alcohols (for example sorbitol), alkyl glucosides (for example methyl glucoside, butyl glucoside, lauryl glucoside) and polyglucosides (for example cellulose);
- alkoxylation products of saccharose esters
- mono-, di and trialkyl phosphates and mono-, di- and/or tri-PEG-alkyl phosphates and salts thereof;
- wool wax alcohols;
- polysiloxane/polyalkyl polyether copolymers and corresponding derivatives;
- mixed esters of pentaerythritol, fatty acids, citric acid and fatty alcohol and/or mixed esters of $C_{6-22}$ fatty acids, methyl glucose and polyols, preferably glycerol or polyglycerol,
- polyalkylene glycols and
- glycerol carbonate.

The addition products of ethylene oxide and/or propylene oxide onto fatty alcohols, fatty acids, alkylphenols, glycerol mono-, di-, and triesters and sorbitan mono- and diesters of fatty acids or onto castor oil are known commercially available products. They are homologue mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations. The preferred emulsifiers are described in more detail as follows:

Partial Glycerides

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30, and preferably 5 to 10, mol ethylene oxide onto the partial glycerides mentioned are also suitable.

Sorbitan Esters

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30, and preferably 5 to 10, mol ethylene oxide onto the sorbitan esters mentioned are also suitable.

Polyglycerol Esters

Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyesters are the mono-, di- and triesters of trimethylol propane or pentaerythritol with lauric acid, cocofatty acid, tallow fatty acid, palmitic acid, stearic acid, oleic acid, behenic acid and the like, optionally reacted with 1 to 30 mol ethylene oxide.

Alk(en)yl Oligoglycosides

The alkyl or alkenyl oligoglycosides representing also preferred emulsifiers may be derived from aldoses or ketoses containing 5 or 6 carbon atoms, preferably glucose. Accordingly, the preferred alkyl and/or alkenyl oligoglycosides are alkyl or alkenyl oligoglucosides. These materials are also known generically as "alkyl polyglycosides" (APG). The alk (en)yl oligoglycosides according to the invention correspond to formula (II):

$$R^5O[G]_p \qquad (II)$$

wherein $R^5$ is an alkyl or alkenyl radical having from 6 to 22 carbon atoms, G is a sugar unit having 5 or 6 carbon atoms and p is a number from 1 to 10. The index p in general formula (II) indicates the degree of oligomerisation (DP degree), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is mostly a broken number. Alk(en)yl oligoglycosides having an average degree of oligomerisation p of 1.1 to 3.0 are to preferably used. Alk(en)yl oligoglycosides having a degree of oligomerisation below 1.8 and, more particularly, between 1.4 and 1.7 are preferred from the applicational point of view. The alkyl or alkenyl radical $R^5$ may be derived from primary alcohols containing 4 to 22 and preferably 8 to 16 carbon atoms. Typical examples are butanol, caproic alcohol, caprylic alcohol, capric alcohol, undecyl alcohol, lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and technical mixtures thereof such as are formed, for example, in the hydrogenation of technical fatty acid methyl esters or in the hydrogenation of aldehydes from Roelen's oxo synthesis. Alkyl oligoglucosides based on hydrogenated $C_8$-$C_{16}$ coconut oil alcohol having a DP of 1 to 3 are preferred. Also suitable are alkoxylation products of alkyl oligoglucosides, for example adducts of 1 to 10 moles ethylene oxide and/or 1 to 5 moles propylene oxide to $C_8$-$C_{10}$ or $C_{12}$-$C_{18}$ alkyl oligoglucoside having a DP between 1.2 and 1.4.

Miscellaneous Emulsifiers

Typical anionic emulsifiers are aliphatic $C_{12-22}$ fatty acids such as palmitic acid, stearic acid or behenic acid, for example, and $C_{12-22}$ dicarboxylic acids such as azelaic acid or sebacic acid, for example. Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —$SO_3H$— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

Solvents

Suitable solvents encompass water and polyols, such as glycerol, ethylene glycol or propylene glycol, preferentially less polar solvents such as 1-methylpyrrolidin-2-one (NMP), dimethylsulfoxide (DMSO), carbonates such as diethyl carbonate, esters e.g. 2-ethylhexyl lactate, ketones such as cyclohexanone, most preferentially unpolar solvents such fatty acid dimethyl amides, other amides e.g. N,N-Dimethylformamide, xylene or commercial destillates like Solvesso 100, 150, or 200.

Formulations

Suitable formulations encompass liquid and solid formulations e.g. SL and WG, respectively (see Pesticide Manual, ibid., p. 1231 for details about formulation types), preferentially those containing an non-polar phase e.g. EW, SE, OD, most preferentially EC and SC.

Agricultural Compositions

Typically, agricultural compositions encompassed by the present invention comprise
(a) about 0.1 to 50, preferably about 1 to 30 and more preferably 5 to 30% b.w. alkoxylation products according to general formula (I),
(b) about 20 to 99.9, preferably about 30 to 80 and more preferably 40 to 60% b.w. biocides,
(c) 0 to about 20, preferably about 1 to 10% b.w. oil components,
(d) 0 to about 10, preferably about 1 to 5% b.w. emulsifiers, and
(e) 0 to about 50, preferably about 5 to 35% b.w. solvents
on condition that the amounts add to 100% b.w.

INDUSTRIAL APPLICATION

Another embodiment of the present invention refers to a method for treating plants, in which a composition as claimed before is sprayed onto the plants or onto the immediate environment of the plants or in the alternative a method for treating seeds, in which a composition as claimed before is used as a seed coating, which is characterised that the biocide is an insecticide, miticide, fungicide, nematicide, or rhodenticide.

Further embodiments of the present invention refer to the use of the alkoxylation products according to general formula (I)
as built-in additive or adjuvant i.e. part of a concentrate to be diluted with water prior to an application on the target crop, or
as tank mix adjuvant or additive i.e. separate addition of a pesticide formulation to the spray tank, or
they also can be brought into the market as ready-to-use dilutions

EXAMPLES

Greenhouse Trials

Examples 1 to 5, Comparative examples C1 to C17

Opus SC125 (epoxiconazole), was tested to control barley powdery mildew (BPM) in a curative greenhouse trial, Amistar SC 250 (azoxystrobin) in a protective trial. In each case, barley was cultivated in pots for three weeks.

Curative Trial with Opus:

Inoculation of the leaves with powdery mildew (*Blumeria graminis* f sp. *hordei*) was done 2 days prior to application to test Opus' curative action. From the stem, leaf segments were cut off with a length of 10 cm using the flag leaf (F) and 2nd leaf (F-1). Altogether, 15 leaves of each were placed on benzimidazol agar. The concentration of Opus for the leaf application was 10 g/ha. Assessment 14 days after treatment (14 DAT) of the efficacy against powdery mildew was done by counting the mildew pustules per leaf on a length of 7 cm.

Protective Trial with Amistar:

5 h after application, leaf segments were cut off at a length of 7 cm from the stem.13 leafs of the F and F-1 leaf were placed on agar. After the inoculation, the incubation time was 10 d.

All alkoxylation products were tested at a rate of 50 ml/ha. Two different technical grade oleyl alcohols were used as starting materials: oleyl alcohol having a iodine value (IV) of 55 (comprising about 40% b.w. saturated species) and oleyl alcohol having a iodine value of 95 (comprising about 5% b.w. saturated species). The results are reflected in the following Tables 1 and 2. Examples 1 to 5 illustrate the invention, examples C1 to C17 are shown for comparison.

TABLE 1

Curative action of alkoxylation products with Opus SC 125 to control BPM

| Example | Additives | Infection rate powdery mildew [%] |
|---|---|---|
| Control | None | 50 |
| 1 | Oleylalcohol + 20EO + acetate (anhydride)(IV = 55) | 23 |
| 2 | Oleylalcohol + 20EO + acetate (anhydride)(IV = 95) | 41 |
| C1 | Oleylalcohol + 2EO (IV = 55) | 46 |
| C2 | Oleylalcohol + 5EO (IV = 55) | 43 |
| C3 | Oleylalcohol + 20EO (IV = 55) | 39 |
| C4 | Oleylalcohol + 3EO (IV = 95) | 48 |
| C5 | Oleylalcohol + 5EO (IV = 95) | 48 |
| C6 | Oleylalcohol + 10EO (IV = 95) | 46 |
| C7 | Oleylalcohol + 10EO + butyl (IV = 95) | 43 |
| C8 | Oleylalcohol + 4EO + 16PO (IV = 95) | 48 |
| C9 | Oleylalcohol + 20EO + butyl (IV = 95) | 45 |
| C10 | Oleylalcohol + 20EO + methyl (IV = 95) | 52 |

Table 1 gives the lowest infection rate of powdery mildes in barley with example 1 i.e. products according to the present invention.

TABLE 2

Protective action of alkoxylation products with Amistar SC 250 to control BPM

| Example | Additives | Infection rate powdery mildew [%] |
|---|---|---|
| Control | None | 40 |
| 3 | Oleylalcohol + 20EO + acetate (anhydride)(IV = 55) | 5 |
| 4 | Oleylalcohol + 20EO + acetate (anhydride)(IV = 95) | 21 |
| 5 | Oleylalcohol + 20EO + 1BO (IV = 95) | 17 |
| C11 | Oleylalcohol + 2EO (IV = 55) | 35 |
| C12 | Oleylalcohol + 5EO (IV = 55) | 24 |
| C13 | Oleylalcohol + 20EO (IV = 55) | 30 |
| C14 | Oleylalcohol + 3EO (IV = 95) | 35 |
| C15 | Oleylalcohol + 10EO + butyl (IV = 95) | 40 |
| C16 | Oleylalcohol + 4EO + 16PO (IV = 95) | 24 |
| C17 | Oleylalcohol + 20EO + butyl (IV = 95) | 25 |

As shown in Table 2, the lowest infection rate were determined with examples 3-5 i.e. products according to the present invention.

Surface Tension

Examples 6 to 8, Comparative examples C18 to C22

Definition of "quasistatic": Static or equilibrium surface tension at an air-liquid interface can be determined by the Du Noüy ring method, the Wilhelmy plate etc. When it comes to measuring polymers, byproducts with low molecular weight can create agglomerates at the surface and lead to artifacts suggesting very low surface tensions. To avoid such problems, a dynamic method is used but the frequency is reduced to 0.1 Hz or less, thus close enough to equilibrium conditions. Foam potential was tested with SITA foam tester R-2000, available from SITA Messtechnik GmbH, Gostritzer Str. 61-63, 01217 Dresden, Germany, at an aqueous concentration of 0.1% in CIPAC water D. Dynamic surface tension was determined with the Krüss Bubble Pressure Tensiometer BP2, available from Krüss GmbH, Borsteler Chaussee 85-99, 22453 Hamburg, Germany, at a bubble frequency of 0.1 Hz, at 20° C., and at an aqueous concentration of 0.25%. Contact angles were tested at 0.25% on Parafilm with Krüss DSA 100. The results are compiled in Table 3.

TABLE 3

Foam pontential, contact angle and surface tension

| Example | Additives | Foam height after 1 min [cm] | Contact angle [° on Parafilm] | Surface tension [mN/m] |
|---|---|---|---|---|
| Control | None | — | | 73 |
| 6 | Oleylalcohol + 10EO + acetate (anhydride)(IV = 95) | 150 | 58 | 39 |
| 7 | Oleylalcohol + 20EO + acetate (anhydride)(IV = 55) | — | 70 | 44 |
| 8 | Oleylalcohol + 20EO + acetate (anhydride)(IV = 95) | 120 | 76 | 44 |
| 9 | Oleylalcohol + 20EO + 1BO (IV = 95) | 160 | 73 | 44 |
| C18 | Oleylalcohol + 5EO (IV = 55) | 190 | 71 | 51 |
| C19 | Oleylalcohol + 20EO (IV = 95) | 170 | 75 | 44 |
| C20 | Oleylalcohol + 10EO + butyl (IV = 95) | 93 | — | 34 |
| C21 | Oleylalcohol + 4EO + 16PO (IV = 95) | — | 67 | 41 |
| C22 | Oleylalcohol + 20EO + butyl (IV = 95) | 160 | 69 | 39 |

Compared with example C19, which is regarded as benchmark, the foam potential within a series of homologues can be influenced by end capping the terminal hydroxy group: Adding a butyl end group or using butylene oxide as terminal group reduces the foam slightly, however, the largest reduction is observed with an acyl end group (example 8). Within a series of homologues i.e. all oleyl alcohols with 20 EO and IV=95, butyl end capped products C20 and C22 give the lowest surface tension i.e. below 40 mN/m. Clearly, the lowest contact angle was determined with example 6. Findings of example 7 are comparable with C21 and C22.

CONCLUSION

The biological tests were designed to differentiate between two mode of actions i.e. a protective mode with Amistar (azoxystrobin) and a curative mode with Opus (epoxiconazole). Since Oleyl+20EO+acetate (IV=55) gave in both tests the best enhancements of fungicidal performance, it shows how versatile the products of the present inventions are. In both cases, wetting of the substrate e.g. leaves is of crucial importance. Surprisingly, acetyl end capped products show low contact angles. For good penetration, a low quasistatic surface tension is a good indication for performance. In this regard, products of the present inventions do not offer special properties. Nevertheless, a person skilled in the art would not have expected superior biological performance by the given contact angles and surface tensions. Additionally, end capping with an acyl group reduces the foam potential compared to the precursor i.e. having a terminal hydroxy group.

What is claimed is:

1. An agrochemical composition comprising a biocide and an alkoxylation product according to formula (I)

$$R^1\text{—O-}[EO]_n[BO]R^3 \quad (I)$$

wherein
- $R^1$ is an oleyl radical;
- [EO] is ethylene oxide;
- [BO] is butylene oxide;
- $R^3$ is hydrogen; and
- n is an integer between 5 and 30.

2. The composition according to claim 1 wherein n is an integer between 10 and 20.

3. The composition of claim 1, where n is 20.

4. The composition according to claim 1, wherein the biocide is selected from the group consisting of herbicides, insecticides, fungicides, miticides, and plant growth promoters.

5. The composition according to claim 1, wherein the biocide is selected from those having a systemic or semi-systemic mode of action.

6. The composition according to claim 1, wherein the biocide has a water solubility of less than 600 ppm.

7. The composition according to claim 1 wherein the composition comprises
   (a) 0.1 to 50% b.w. alkoxylation products according to formula (I),
   and wherein the composition further comprises
   (b) 20 to 99.9% b.w. biocides,
   (c) 0 to 20% b.w. oil components,
   (d) 0 to 10% b.w. emulsifiers, and
   (e) 0 to 50% b.w. solvents
with the proviso that the amounts add to 100% b.w.

8. A method for treating plants, the method comprising spraying the composition of claim 1 onto plants or onto the immediate environment of the plants.

9. The method of claim 8, wherein n is an integer between 10 and 20.

10. The method of claim 8, wherein n is 20.

11. A method for treating seeds, the method comprising coating a seed with the composition of claim 1, wherein said biocide is selected from the group consisting of insecticides, miticides, fungicides, nematicides and rhodenticides.

12. A method of making the agrochemical composition of claim 1, the method comprising obtaining the alkoxylation product of formula (I), and mixing the alkoxylation product with the biocide, wherein the alkoxylation product is effective as an adjuvant.

13. A method of making the agrochemical composition of claim 1, the method comprising obtaining the alkoxylation product of formula (I), and adding the alkoxylation product to a tank as a tank mix additive, the tank comprising the biocide.

* * * * *